United States Patent [19]

Inglett

[11] Patent Number: 4,996,063
[45] Date of Patent: Feb. 26, 1991

[54] METHOD FOR MAKING A SOLUBLE DIETARY FIBER COMPOSITION FROM OATS

[75] Inventor: George F. Inglett, Peoria, Ill.

[73] Assignee: The United States of America, as represented by the Secretary of Agriculture, Washington, D.C.

[21] Appl. No.: 373,978

[22] Filed: Jun. 30, 1989

[51] Int. Cl.$^5$ .............................................. A23L 1/105
[52] U.S. Cl. ........................................ 426/21; 426/28; 426/31; 426/577; 426/804
[58] Field of Search ...................... 426/21, 28, 31, 804, 426/577

[56] References Cited

U.S. PATENT DOCUMENTS

| | | | |
|---|---|---|---|
| 1,204,869 | 11/1916 | Heuser | 426/31 |
| 1,543,458 | 6/1925 | Takamine | 426/28 |
| 1,564,181 | 12/1925 | Kellogg | 426/28 |
| 1,885,411 | 11/1932 | Brown | 426/31 |
| 3,395,019 | 7/1968 | Kviesitis | 426/31 |
| 3,573,061 | 3/1971 | Globe | 426/21 |
| 4,143,172 | 3/1979 | Mitchell | 426/577 |
| 4,200,694 | 4/1980 | Ishii | 426/577 |
| 4,282,319 | 8/1981 | Conrad | 426/28 |
| 4,388,337 | 6/1983 | Cawdron | 426/577 |
| 4,540,585 | 9/1985 | Priegnitz | 426/28 |
| 4,582,712 | 4/1986 | Gonsalves | 426/577 |
| 4,619,831 | 10/1986 | Sharma | 426/104 |
| 4,656,040 | 4/1987 | Fulger | 426/28 |
| 4,680,189 | 7/1987 | Schumacher | 426/804 |
| 4,710,386 | 12/1987 | Fulger | 426/28 |
| 4,710,390 | 12/1987 | Schumacher | 426/804 |
| 4,804,545 | 2/1989 | Goering | 426/28 |
| 4,814,172 | 3/1989 | Chavkin et al. | 426/804 |
| 4,834,989 | 5/1989 | Bolles | 426/28 |
| 4,857,356 | 8/1989 | Reinl | 426/28 |

OTHER PUBLICATIONS

Rasper 1979 Chemical and Physical Properties of Dietary Cereal Fiber, Jan., pp. 40–44.

Primary Examiner—Carolyn Paden
Attorney, Agent, or Firm—M. Howard Silverstein; John D. Fado; Curtis P. Ribando

[57] ABSTRACT

Water-soluble dietary fiber compositions can be prepared by treatment of oat-milled products with α-amylases. The dietary fiber compositions are colorless and devoid of inherent undesirable flavors and are, therefore, uniquely suitable for use in a variety of foods.

10 Claims, No Drawings

METHOD FOR MAKING A SOLUBLE DIETARY FIBER COMPOSITION FROM OATS

BACKGROUND OF THE INVENTION

1. Field of the Invention

Dietary fiber is considered to be the soluble and insoluble components of food that are not digested by enzymes in the human gastrointestinal tract. The primary sources of dietary fiber include such cell wall materials as cellulose, hemicelluloses, lignin, and pectins, along with gums and mucilages. Dietary fiber has been considered an important food component since early times. Recently, Burkitt et al. [Lancet 2: 1408–1411 (1972)] concluded that dietary fiber has a role in the prevention of certain large-intestine diseases, including cancer of the colon and diverticulitis. Diets containing large amounts of dietary fiber lead to stools that are softer and larger, and bowel movements are generally more frequent. Burkitt also mentioned that the serum cholesterol rises when dietary fiber is removed from the diet, and that eating a fiber-rich diet lowers serum cholesterol. Trowell [Am. J. Clin. Nutr. 25: 464–465 (1972)] reached a similar conclusion regarding the relationship between fiber and health benefits.

It is now known that all dietary fiber is not the same and that different fibers provide different health benefits. For example, wheat bran is very rich in insoluble dietary fiber (mainly cellulose and hemicelluloses) and is excellent for decreasing the transit time of food through the digestive tract [Anderson et al., Am. J. Clin. Nutr. 32: 346–363 (1979)]. Some fibers are reported to reduce total plasma cholesterol [Munoz et al., Am. J. Clin. Nutr. 32: 580–592 (1979)]. This invention relates to a novel food composition from oats that provides soluble dietary fiber useful as a functionally and nutritionally advantageous ingredient for a variety of food products.

2. Description of the Prior Art

The first indication of serum cholesterol lowering by rolled oats was observed in rats by Degroot et al. [Lancet 2: 303–304 (1963)]. Fisher et al. [Pro. Soc. Exp. Biol. Med. 126: 108–111 (1967)] report that the fiber fraction of oats is responsible for its unique effects on cholesterol. Over the years, numerous experiments with animals have shown that oat fiber has a strong hypocholesterolemic effect. Anderson et al. [Am. J. Clin. Nutr. 34: 824–829 (1981); 40: 1146–1155 (1984)] have confirmed hypocholesterolemic effects of oats in humans.

It is the soluble fiber that is effective in lowering cholesterol levels. Oatmeal, or rolled oats, and especially oat bran are the best sources of this soluble fiber. Moreover, oat fiber reduces the amount of low density lipoprotein (LDL) without lowering the beneficial high density lipoprotein (HDL). In fact, Anderson et al. [66th Annual Meeting, Am. Assoc. Cer. Chemists, Abstract No. 112 (1981)] teach that oat bran fed to humans can reduce LDL 58% while increasing HDL 82%. Other water-soluble fibers, such as pectin and guar gum, can lower serum cholesterol, but they are frequently accompanied by undesirable side effects such as nausea and vomiting. The results of another study by Anderson et al. (supra, 1984) indicate that oat bran diets decrease total serum cholesterol 19% and LDL 23% and that oat bran increases bile acid excretion 65%. These studies clearly document the hypocholesterolemic effects in humans of oat products which are rich in soluble fiber.

In the art of starch hydrolysis, it is known that starch can be hydrolyzed by acids or enzymes to give a variety of products with properties depending on the degree of conversion. Acid conversions are known to give uniform distribution of hydrolysate fragments because of the random cleavages of the starch molecule, whereas enzymes result in variations in amounts of the different oligomer fragments [Inglett, J. Food Biochem. 11: 249–258(1987)]. Various amylolytic enzymes are used in the thinning or liquefaction of starch and in the production of low conversion starch hydrolysates which are known in the trade as maltodextrins or corn syrup solids, depending upon the degree of hydrolysis (Morehouse, U.S. Pat. No. 3,663,369). It is also recognized that specific maltodextrins can be prepared at a D.E. within the range of 10–13 (Coker, U.S. Pat. No. 4,447,532). The starches used to prepare maltodextrins are obtained primarily from the wet milling of corn. Other sources of starch for commercial products are tapioca, potato, and rice.

Whole cereal flours have also been subjected to starch-hydrolyzing conditions and have yielded, for example, a whole-grain hydrolyzed product (Conrad, U.S. Pat. No. 4,377,602) and a ready-to-eat, enzyme-saccharified cereal (Fulger et al., U.S. Pat. No. 4,710,386). Ronai (U.S. Pat. No. 3,640,729) arrives at a similar product by adding prehydrolyzed starch to oat flour to yield an instant oat cereal product.

SUMMARY OF THE INVENTION

I have now discovered that water-soluble dietary fiber compositions can be recovered from milled products of oats such as oat bran and oat flour after enzymatic hydrolysis of these substrates with $\alpha$-amylases. The resulting soluble dietary fiber compositions separated with the soluble hydrolyzate fractions are colorless and devoid of inherent undesirable flavors. The soluble fiber compositions are, therefore, uniquely suitable for use in a variety of foods such as dairy products, dairy product substitutes, high-soluble fiber bakery products, frozen foods, yoghurt, snacks, confectioneries, coatings, dietary-fiber beverages, and breakfast foods.

In accordance with this discovery, it is an object of the invention to provide a novel source of water-soluble dietary fiber compositions for incorporation into ingestible formulations.

Another object of the invention is to provide a process of producing water-soluble dietary fiber compositions suitable for human consumption.

It is also an object of the invention to provide a novel protein-rich ingredient for food or animal feed compositions.

Other objects and advantages of this invention will become readily apparent from the ensuing description.

DETAILED DESCRIPTION OF THE INVENTION

Suitable substrates contemplated for use in the invention include milled products of oats such as oat bran and oat flour. The substrate is slurried in a sufficient amount of water to give a concentration in the range of about 10–40% by weight. The water should contain a suitable calcium salt in an amount sufficient to stabilize the subsequently added $\alpha$-amylase [preferably about 25–50 parts per million (ppm) of calcium]. The slurried substrate may be gelatinized prior to enzymatic treatment, using any method known in the art. The pH of the ungelatinized slurry or the gelatinized dispersion is adjusted to about 5.5-7.5, preferably about 6.0, with sodium hydroxide or other alkali, and the α-amylase is added.

It is advantageous to use thermostable α-amylases referred to as 1,4-α-D-glucan glucanohydrolases and having the essential enzymatic characteristics of those produced by the *Bacillus stearothermophilus* strains ATCC Nos. 31,195; 31,196; 31,197; 31,198; 31,199; and 31,783. These strains are described in U.S. Pat. No. 4,284,722, which is herein incorporated by reference. Other sources of this enzyme include organisms such as *B. subtilis* which have been genetically modified to express the thermostable α-amylase of *B. stearothermophilus* as described in U.S. Pat. No. 4,493,893, herein incorporated by reference. These enzymes are available commercially under the name "Enzeco Thermolase" (Enzyme Development, Div., Biddle Sawyer Corp., New York, NY).

Other suitable α-amylases are those having the essential enzymatic characteristics of those produced by *B. licheniformis* var. as described in U.S. Pat. No. 4,717,662 and 4,724,208, herein incorporated by reference. These enzymes are available commercially under the name "Takalite" (Miles Laboratories, Inc., Biotech Products Division, Elkhart, IN). Of course, any α-amylase which is useful in the thinning of the oat starch is contemplated for use herein.

The conditions of enzyme treatment, including the enzyme concentration and the time and temperature of reaction, are selected to achieve liquefaction of the starch in the substrate to the extent that the soluble fiber bound by the cellular matrix is substantially completely liberated into solution. When using a thermostable α-amylase, a preferred treatment temperature is in the range of 70°-100° C., preferably about 95° C. At these temperatures, gelatinization of the starch in the substrate occurs concurrently with the hydrolysis. The duration of the treatment at the desired conversion temperature depends on the desired product properties and will generally range from about 10-60 min.

After completion of the enzymatic hydrolysis, the enzyme is inactivated, such as by passing the mixture through a steam injection pressure cooker at a temperature of about 140° C. Alternatively, the enzyme may be inactivated by acidification (pH 3.5-4.0) at 95° C. for about 10 min. Optional neutralization with alkali increases the salt concentration of the product. After the enzyme has been inactivated, the soluble fraction comprising the soluble oat fiber and maltooligosaccharides is separated from the insoluble residue by centrifugation. Water is then removed from the soluble fraction in the centrifugate by any of a variety of conventional techniques, and the soluble oat fiber product of the invention is recovered.

It was surprising to find that the products of this invention are readily obtainable in a colorless, white, and smooth-textured form, devoid of inherent undesirable color, flavor, and grittiness associated with the starting materials. They are remarkably adapted for use as functional and nutritional components of many foods including dairy products, in which consumer preference dictates the virtual absence of the flavor, color, and grittiness inherent to the starting substrate and to most dietary fibers currently marketed.

Characterization of the insoluble residue from the conversion mixture (supra) reveals a high proportion of protein. The protein is believed to complex with the lipid and to become insolubilized by heat denaturation. The residue also contains the insoluble fiber and the majority of the flavor and color components. This by-product, therefore, has potential as an ingredient in foods or animal feeds and is considered an ancillary asset to the inventive process.

The following examples are presented only to further illustrate the invention and are not intended to limit the scope of the invention which is defined by the claims.

All percentages herein disclosed are by weight unless otherwise specified.

EXAMPLES 1-4

Effect of Process pH.

For each preparation, 100 g (dry basis) of oat flour (The Quaker Oats Company, Cedar Rapids, IA) was slurried in 400 ml of water containing 25 ppm of calcium (0.09 g/l $CaCl_2.2H_2O$) and gelatinized by passage through a steam injection cooker at 138°-143° C. (30-40 psi of steam pressure). The gelatinized mixture was collected in a container, and the pH was adjusted with 1.0N sodium hydroxide as desired (Table I). "Enzeco Thermolase" (supra) was added to the mixture at 95° C. in an amount sufficient to provide 24 units per gram of oat flour, where 1 unit of amylase activity is the amount of enzyme required to hydrolyze 10 mg of starch per minute under specified conditions [Enzyme Development Div., Biddle Sawyer Corp., New York, NY, Technical Bulletin No. 20 (Revised 7/86)]. After 20 min of stirring at 95° C., the starch was liquefied, and the enzyme was inactivated by passing the mixture through a steam injection cooker (supra). The mixture was then allowed to cool to about 70° C., and it was centrifuged 30 min at 5000 rpm. The water-soluble fiber product in the supernatant solution was recovered by decanting the solution and freeze-drying. The insoluble residue obtained from centrifuging was removed and air-dried. The results in Table I show that the higher pH's (9 and 11) are accompanied by undesirably high levels of protein in the soluble products and decreased protein amounts in the insoluble residues.

EXAMPLES 5-7

Effect of Enzyme Level.

Compositions were prepared as described in Examples 1-4 except that the starting oat flour was obtained from National Oats Company (Cedar Rapids, IA), the process pH was 6.0 for all preparations, and enzyme was added in varying amounts as reported in Table II. The DP distribution of starch oligomers in the products was determined by high-pressure liquid chromatography (Inglett, supra). The data in Table II show that lower enzyme amounts result in higher DP starch oligomers.

TABLE I

| Example | pH | Product-residue ratio | Protein (%) Soluble product | Protein (%) Insoluble residue |
|---|---|---|---|---|
| 1 | 6 | 2.79 | 3.3 | 66.1 |
| 2 | 7 | 2.47 | 3.1 | 44.1 |
| 3 | 9 | 5.43 | 13.9 | 35.5 |
| 4 | 11 | 15.3 | 17.7 | 16.6 |

TABLE II

| Example | Enzyme concentration (units/g substrate) | DP > 9 (% of total oligomers) |
| --- | --- | --- |
| 5 | 6 | 93.0 |
| 6 | 12 | 47.7 |
| 7 | 24 | 36 5 |

EXAMPLE 8

Low Temperature Treatment.

Two hundred grams (dry basis) of oat flour [National Oats Company (supra)] were slurried in 800 ml of water containing 50 ppm of calcium (0.185 g/l $CaCl_2.2H_2O$). The pH of the slurry was adjusted to 6.0 with 1.0N sodium hydroxide, and "Enzeco Thermolase" (supra) was added to the stirred slurry in an amount sufficient to provide 48 units (supra) per gram of oat flour. The temperature was increased to 80° C., and stirring was continued until the starch was liquefied. After 20 min, the pH was adjusted to 4.0 with 1N sulfuric acid, and the mixture was heated at 95° C. for 10 min to inactive the enzyme. The pH was then adjusted to 6.2 with 1N sodium hydroxide, and the soluble product was separated from the insoluble residue following the procedure described in Examples 1–4. The total dietary fiber [Prosky et al., J. Assoc. Off. Anal. Chem. 67: 1044 (1984); 68: 399 (1985)] amounted to 4.8% of the product, compared to 7–8% normally obtained in the products of this invention. Because of the acid inactivation of the enzyme and subsequent neutralization with sodium hydroxide, the sodium content of this soluble product was 5215 microg/g, in contrast to the range of 200–900 µg/g for products having the enzyme inactivated by steam injection cooking.

EXAMPLE 9

Pilot Scale Treatment of Oat Bran

Four kilograms of oat bran [National Oats Company (supra)] was slurried in 8 l of water containing 25 ppm of calcium (supra). The pH of the slurry was adjusted to 6.0 with 1.0N sodium hydroxide, and "Takalite L-340" (supra) was added to the slurry in a large Sigma mixer in an amount sufficient to provide 1632 Modified Wohlgemuth Units (MWU) per gram of substrate, where 1 MWU is that activity which will dextrinize 1 mg of soluble starch to a defined size dextrin in 30 min under specified conditions (Biotech Products Div., Miles Laboratories, Inc., Elkhart, IN). During a period of about 10–15 min, the temperature was increased to about 95° C. with steam heat. After 20 min, the enzyme was inactivated by passing the mixture through a steam injection cooker. The warm slurry was centrifuged at 15,000 rpm by a large "Sharples" centrifuge to separate the soluble components from the insoluble components. The percent oligomer composition of the solubles was: DP>9, 32.3; DP 9, 0; DP 8, 0; DP 7, 1.0; DP 6, 13.0; DP 5, 13.9; DP 4, 6.4; DP 3, 13.0; DP 2, 12.1; DP 1, 5.6.

EXAMPLE 10

Pilot-Scale Treatment of Oat Flour

Six kilograms of oat flour [National Oats Company (supra)] was slurried in 18 l of water containing 25 ppm of calcium (supra). The pH of the slurry was 5.75. After gelatinization by passage of the mixture through a steam injection cooker, the slurry was collected in a 30-gal steam-heated kettle. "Enzeco Thermolase" (supra) was added to the slurry in an amount sufficient to provide 1 unit per gram of oat flour. After 5 min of stirring at 80°–90°, the enzyme was inactivated by passing the slurry through a steam injection cooker (supra). The warm slurry was centrifuged at 15,000 rpm by a large "Sharples" centrifuge to separate the soluble and insoluble components. The products were dried separately on hot rolls. The oligomer composition indicated 98% DP 9 and larger.

EXAMPLE 11

Sensory Evaluation of Oat Fiber-Containing Ice Milks

The soluble oat fiber product of Example 7 and the starting oat flour from which it was obtained (supra), were evaluated as ingredients in ice milks. For each preparation, 484 g of 0.5%-fat milk, 100 g of sugar, 1.9 g of vanilla extract, and 0.4 g of uniodized salt were mixed for 1 min in a blender with the oat products and in the amounts reported in Table III. Each mixture was treated in a 2-qt ice cream mixer (Oster) for 30 min.

An 18-member trained panel experienced in testing cereal products evaluated the ice milk samples for flavor, texture, and overall quality by a modification of the method of Warner et. al. Cereal Chem. 60: 102–106 (1983)], herein incorporated by reference. At each panel session, the testers received a control sample of laboratory-prepared ice cream and two randomized, unidentified ice milk samples. The panelists were instructed to rate the three samples for intensity of the descriptors listed in Table III, using the scales in the Table footnotes. Scores were statistically analyzed for significant differences at the 95% confidence level (P <0.05).

The results in Table III show that the sweetness of the oat-containing samples did not vary significantly from that of the plain ice milk, and two of the oat samples (11D and 11G) did not vary significantly from the ice cream control. The vanilla flavor intensity was highest in the ice cream control, and two of the oat samples (11D and 11F) were not significantly different; all the oat-containing samples ranged between 4.9 and 5.5 except 11G and 11H, which were significantly lower than the others. The creamy flavor intensity also was highest in the ice cream control; next in creamy flavor were the three ice milk samples containing the invention product. Cereal flavor intensity was significantly lower in the three samples containing the invention product than in the three samples containing the starting oat flour, and two of the invention samples were not significantly different from the ice cream control and the ice milk that contained no oat product.

TABLE III[1]

| Sample | Oat ingredient[2] | Flavor intensity[3] | | | | Texture[4] | | | | Overall quality[9] |
| --- | --- | --- | --- | --- | --- | --- | --- | --- | --- | --- |
| | | Sweet | Vanilla | Creamy | Cereal | Viscosity[5] | Graininess[6] | Cohesiveness[7] | Density[8] | |
| 11A | Control (ice cream) | 7.3a | 6.5a | 7.6a | 0a | 1.9a | 1.8a | 5.2a | 7.6a | 8.5a |
| 11B | Plain ice milk (no oat product) Treated | 5.9b | 5.2b | 3.1b | 0.2a | 6.7b | 3.2b | 2.9b | 2.2b | 4.9b |

TABLE III[1]-continued

| Sample | Oat ingredient[2] | Flavor intensity[3] | | | | Texture[4] | | | | Overall quality[9] |
|---|---|---|---|---|---|---|---|---|---|---|
| | | Sweet | Vanilla | Creamy | Cereal | Viscosity[5] | Graininess[6] | Cohesiveness[7] | Density[8] | |
| 11C | Soluble oat fiber (2%) | 5.9b | 5.0b | 4.2c | 0.3a | 7.0b | 2.5b | 3.3b | 3.4c | 5.5b |
| 11D | Soluble oat fiber (5%) | 6.6ab | 5.5ab | 4.3cd | 0.7a | 6.8b | 2.8b | 4.0b | 4.2c | 5.7b |
| 11E | Soluble oat fiber (10%) Untreated | 6.4b | 4.9b | 5.3d | 1.9b | 5.0c | 3.1b | 5.3a | 5.8d | 5.5b |
| 11F | Oat flour (2%) | 6.2b | 5.5ab | 3.6bc | 2.9b | 6.8b | 5.0c | 3.2b | 3.3c | 4.9b |
| 11G | Oat flour (5%) | 6.5ab | 3.6c | 2.7b | 5.9c | 7.5b | 5.9cd | 3.4b | 4.3ce | 3.4c |
| 11H | Oat flour (10%) | 5.5b | 3.8c | 3.5bc | 7.0d | 6.3b | 6.6d | 3.8b | 4.6e | 2.9c |

[1] Values followed by the same letter are not significantly different.
[2] Percentage of added oat ingredient is based on weight of all other ingredients.
[3] Based on a 0–10 scale: 10 = strong; 0 = none.
[4] Based on a 1–10 scale.
[5] 1 = creamy; 10 = icy.
[6] 1 = smooth; 10 = grainy.
[7] 1 = crumbly; 10 = gummy.
[8] 1 = light; 10 = compact.
[9] Based on a 1–10 scale: 10 = excellent; 1 = bad.

The creamiest texture among the ice milks was exhibited by 11E; all the other ice milks did not vary significantly from sample to sample. Graininess was significantly lower in the three invention samples than in the other three oat-containing samples. Cohesiveness of 11E did not vary significantly from that of the ice cream control; all the other ice milks ranged from 2.9–4.0. Density values ranged from a low of 2.2 for the plain ice milk to a high of 7.6 for the ice cream control. Both the invention samples and the other oat samples yielded increasing density with increasing concentration of additive.

The ice milks were significantly lower in overall quality than the ice cream control, and the highest levels of oat flour starting material (11G and 11H) resulted in significantly lower overall quality than that of the other ice milks. The ice milks containing the invention product had the highest scores among the ice milks.

In summary, the soluble oat fiber product of the invention increased the creamy flavor, creamy texture, cohesiveness, and density of ice milks without imparting the inherent cereal flavor and grainy texture of the starting oat flour.

EXAMPLE 12

Sensory Evaluation of Oat Fiber-Containing Milks

The oat materials listed in Table IV were blended into milk and evaluated for flavor characteristics as in Example 11. For each preparation, 300 g of 0.5%-fat milk and 30 g of oat product were mixed for 1 min in a blender, poured into a flask, and swirled before serving to the test panel. Each panelist received a control of 0.5%-fat milk identified as having a milky flavor intensity score of 8, plus two randomized, unidentified test samples. The panelists were instructed to score the three samples for intensity of the descriptors listed in Table IV. Scoring was based on a 0–10 scale (10=strong; 0=none). Scores were statistically analyzed as in Example 11. Values that were not significantly different are followed by the same letter in Table IV. The results reported in the Table show that the soluble oat fiber products of the invention (12E and 12F) had significantly lower cereal flavor intensity scores than the other oat materials.

EXAMPLE 13

Preparation of Yoghurt.

A yoghurt was prepared from retail 2% milk, instant nonfat dry milk, sugar (sucrose), water, potassium sorbate, and the soluble oat fiber obtained in Example 10. A control yoghurt without the fiber was also prepared. Compositions of the starting mixtures are set forth in Table V below. The ingredients were blended together with a wire whip. The resulting mixtures were heated to 185° F. in stainless steel beakers, held at temperature for 30 min, cooled to 110° F., and then inculated with 2% bulk starter (Hansen's CH3 propagated once in 11% nonfat milk). The inoculated mixtures were cultured to a pH of 4.35–4.40 (270 min for the control; 165 min for the test sample). The yoghurt was then stirred, poured into containers, and cooled overnight, achieving a final pH of 4.0–4.2. The samples were evaluated in a Brookfield viscometer Model RVT equipped with a No. 2 spindle at 0.5 rpm and at 50° F. They were also evaluated for sensory properties.

The control was characterized by a viscosity of 48,000 cp and a good yoghurt flavor with smooth texture. The test sample with the oat fiber of Example 10 had a viscosity of 22,400 cp, a slight cereal flavor, and a smooth texture.

TABLE IV

| Sample | Oat product | Flavor intensity | | | |
|---|---|---|---|---|---|
| | | Sweet | Milky | Cereal | Cardboardpaper |
| 12A | Control (0.5% fat milk) | 4.2a | 8.0b | 0 | 0 |
| 12B | Oat flour[1] | 3.5a | 4.8c | 7.3e | 2.8g |
| 12C | Enzyme-treated oat bran[2] | 3.1a | 3.4d | 7.1e | 2.5g |
| 12D | Enzyme-treated oat flour[3] | 4.4a | 4.8c | 6.5e | 2.6g |
| 12E | Soluble oat fiber (invention)[4] | 4.4a | 4.7c | 3.3f | 3.0g |

TABLE IV-continued

| Sample | Oat product | Flavor intensity | | | |
|---|---|---|---|---|---|
| | | Sweet | Milky | Cereal | Cardboardpaper |
| 12F | Soluble oat fiber (invention)[5] | 4.6a | 5.4c | 2.2f | 3.5 |

[1] National Oats Company.
[2] Preparation described in Example 10 without separation of solubles from insolubles.
[3] Oat flour (12B) treated by the procedure of Example 10 without separation of solubles from insolubles.
[4] Obtained from oat flour (12B) by the procedure of Example 1 except that the enzyme was inactivated by pH adjustment instead of steam-injection cooking.
[5] Obtained from Quaker (supra) oat flour by the procedure of Example 6.

TABLE V

| Composition | Control (%) | Example 13 (%) |
|---|---|---|
| Butterfat | 1.00 | 1.00 |
| MSNF[a] | 12.00 | 7.00 |
| Sucrose | 6.00 | 6.00 |
| K-Sorbate | 0.04 | 0.04 |
| Soluble fiber | ... | 5.00 |

[a] Milk solids, nonfat.

It is understood that the foregoing detailed description is given merely by way of illustration and that modification and variations may be made therein without departing from the spirit and scope of the invention.

I claim:

1. A method for producing a water-soluble dietary fiber composition comprising treating an aqueous dispersion of a gelatinized, milled, oat substrate with an α-amylase under conditions which will hydrolyze the substrate and yield a soluble fraction and an insoluble fraction, separating said soluble fraction from said insoluble fraction, and recovering from said soluble fraction said water-soluble dietary fiber substantially free of water-insoluble fiber.

2. The method as described in claim 1 wherein the solids content of said oat substrate dispersion is in the range of about 10-40%.

3. A dietary fiber product produced by the method of claim 2.

4. The method as described in claim 1 wherein said oat substrate is selected from the group consisting of oat flour and oat bran.

5. A dietary fiber product produced by the method of claim 4.

6. The method as described in claim 1 wherein said treatment is performed at a temperature in the range of about 70°-100° C.

7. A dietary fiber product produced by the method of claim 6.

8. The method as described in claim 1 wherein said α-amylase is a thermostable α-amylase and said oat substrate is gelatinized concurrently with said hydrolysis.

9. A dietary fiber product produced by the method of claim 8.

10. A dietary fiber product produced by the method of claim 1.

* * * * *

UNITED STATES PATENT AND TRADEMARK OFFICE
CERTIFICATE OF CORRECTION

PATENT NO. : 4,996,063
DATED : February 26, 1991
INVENTOR(S) : George E. Inglett It is certified that error appears in the above-identified patent and that said Letters Patent is hereby corrected as shown below:

On the title page, correct the inventor's name from "George F. Inglett" to read -- George E. Inglett -- .

Signed and Sealed this

Twenty-fifth Day of August, 1992

Attest:

DOUGLAS B. COMER

Attesting Officer

Acting Commissioner of Patents and Trademarks